(12) United States Patent
Parins et al.

(10) Patent No.: US 7,747,314 B2
(45) Date of Patent: Jun. 29, 2010

(54) DISTAL ASSEMBLY FOR A MEDICAL DEVICE

(75) Inventors: David J. Parins, Corcoran, MN (US); Peter Skujins, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 550 days.

(21) Appl. No.: 10/748,933

(22) Filed: Dec. 30, 2003

(65) Prior Publication Data

US 2005/0148901 A1 Jul. 7, 2005

(51) Int. Cl.
*A61M 25/00* (2006.01)
(52) U.S. Cl. .................. 600/434; 600/433; 600/435; 600/585; 604/164.13
(58) Field of Classification Search .......... 600/433, 600/434, 435, 585; 604/164.13
See application file for complete search history.

(56) References Cited

U.S. PATENT DOCUMENTS

| | | | |
|---|---|---|---|
| 3,174,851 A | 3/1965 | Buehler et al. | |
| 3,351,463 A | 11/1967 | Rozner et al. | |
| 3,753,700 A | 8/1973 | Harrison et al. | |
| 4,676,249 A * | 6/1987 | Arenas et al. | 600/434 |
| 4,732,163 A * | 3/1988 | Bonello et al. | 600/585 |
| 4,757,827 A * | 7/1988 | Buchbinder et al. | 600/585 |
| 4,815,478 A * | 3/1989 | Buchbinder et al. | 600/585 |
| 5,040,543 A * | 8/1991 | Badera et al. | 600/585 |
| 5,063,935 A * | 11/1991 | Gambale | 600/585 |
| 5,065,769 A | 11/1991 | de Toledo | |
| 5,069,226 A | 12/1991 | Yamauchi et al. | |
| 5,084,022 A | 1/1992 | Claude | |
| 5,178,159 A * | 1/1993 | Christian | 600/585 |
| 5,211,636 A * | 5/1993 | Mische | 604/264 |
| 5,213,111 A | 5/1993 | Cook et al. | |
| 5,217,026 A * | 6/1993 | Stoy et al. | 600/585 |
| 5,228,453 A | 7/1993 | Sepetka | |
| 5,234,437 A * | 8/1993 | Sepetka | 606/108 |
| 5,238,004 A | 8/1993 | Sahatjian et al. | |
| 5,259,393 A | 11/1993 | Coroso, Jr. et al. | |
| 5,267,574 A | 12/1993 | Viera et al. | |
| 5,313,957 A * | 5/1994 | Little | 600/561 |
| 5,333,620 A | 8/1994 | Moutafis et al. | |
| 5,345,945 A * | 9/1994 | Hodgson et al. | 600/585 |
| 5,365,944 A * | 11/1994 | Gambale | 600/585 |
| 5,372,144 A * | 12/1994 | Mortier et al. | 600/585 |
| 5,452,726 A * | 9/1995 | Burmeister et al. | 600/585 |
| 5,460,187 A | 10/1995 | Daigle et al. | |
| 5,498,250 A | 3/1996 | Prather | |
| 5,517,989 A * | 5/1996 | Frisbie et al. | 600/585 |
| 5,571,073 A | 11/1996 | Castillo | |
| 5,622,184 A | 4/1997 | Ashby et al. | |
| 5,673,707 A | 10/1997 | Chandrasekavan | |
| 5,772,609 A | 6/1998 | Nuyen et al. | |
| 5,876,356 A | 3/1999 | Viera et al. | |

(Continued)

*Primary Examiner*—Max Hindenburg
*Assistant Examiner*—Rene Towa
(74) *Attorney, Agent, or Firm*—Crompton, Seager & Tufte, LLC

(57) ABSTRACT

Alternative designs, materials and manufacturing methods for guidewires. Some embodiments pertain to a composite guidewire having proximal and distal section, and a connector adapted and configured for permanently joining the proximal section to the distal section. In some embodiments, at least one of the sections is made of a linear-elastic nickel-titanium alloy. Several alternative guidewire tip designs including coiled safety/shaping structures are also disclosed.

14 Claims, 4 Drawing Sheets

U.S. PATENT DOCUMENTS

| | | | |
|---|---|---|---|
| 5,957,865 A | 9/1999 | Backman et al. | |
| 5,971,975 A | 10/1999 | Mills et al. | |
| 5,984,877 A | 11/1999 | Fleischhacker, Jr. | |
| 5,993,424 A * | 11/1999 | Lorenzo et al. | 604/164.13 |
| 6,056,702 A | 5/2000 | Lorenzo | |
| 6,113,557 A * | 9/2000 | Fagan et al. | 600/585 |
| 6,139,510 A | 10/2000 | Palermo | |
| 6,329,069 B1 | 12/2001 | Azizi et al. | |
| 6,500,130 B2 | 12/2002 | Kinsella et al. | |
| 6,508,803 B1 | 1/2003 | Horikawa et al. | |
| 6,520,923 B1 | 2/2003 | Jalisi | |
| 6,544,231 B1 * | 4/2003 | Palmer et al. | 604/165.01 |
| 6,673,025 B1 * | 1/2004 | Richardson et al. | 600/585 |
| 2003/0069520 A1 | 4/2003 | Skujins et al. | |
| 2003/0069521 A1 | 4/2003 | Reynolds et al. | |
| 2003/0139689 A1 | 7/2003 | Shturman et al. | |
| 2004/0142643 A1 | 7/2004 | Miller et al. | |
| 2004/0167441 A1 | 8/2004 | Reynolds et al. | |
| 2004/0167442 A1 | 8/2004 | Shireman et al. | |

* cited by examiner

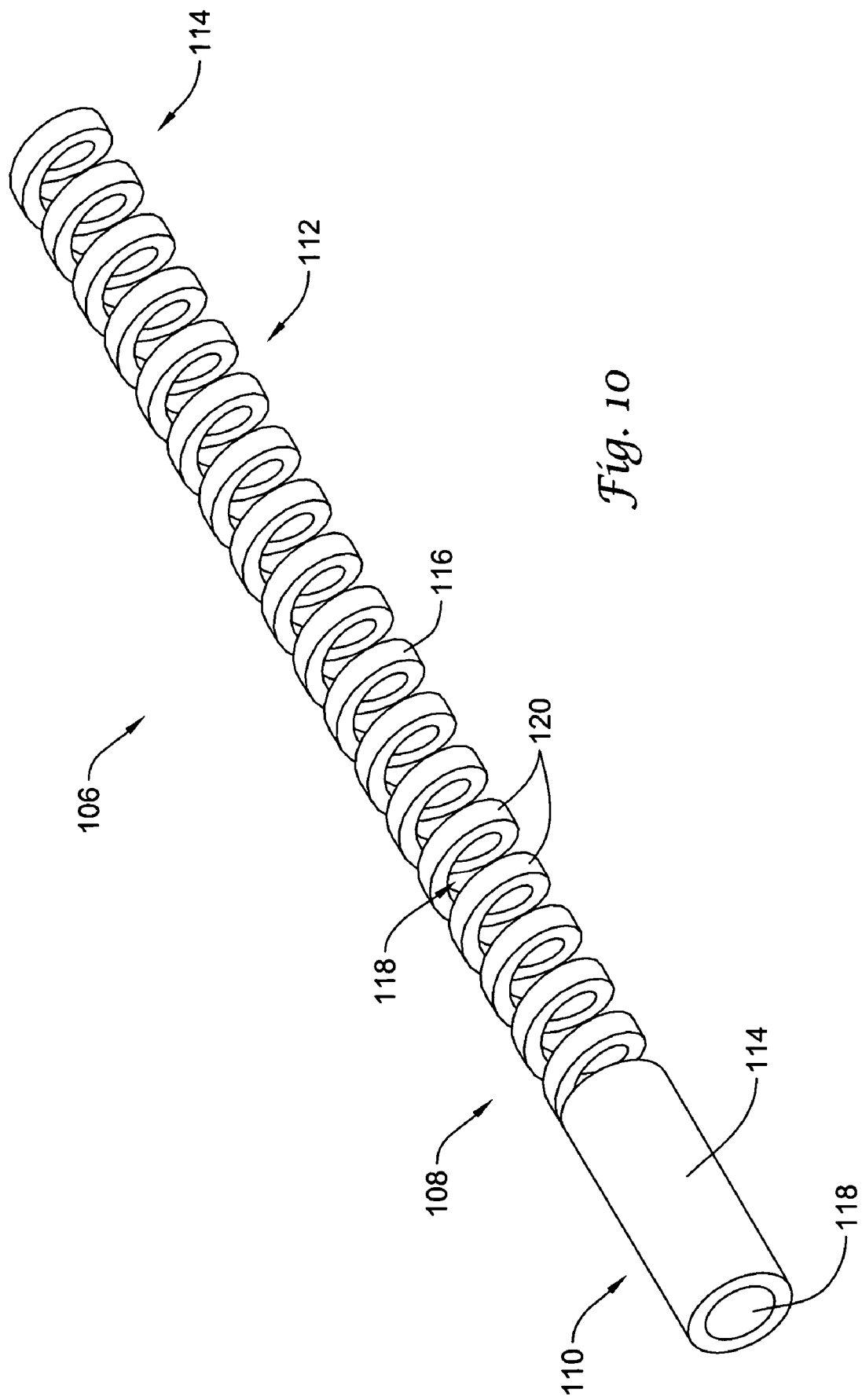

DISTAL ASSEMBLY FOR A MEDICAL DEVICE

TECHNICAL FIELD

The invention generally pertains to medical devices, such as guidewires, catheters, and the like.

BACKGROUND

A wide variety of medical devices, such as guidewires, catheters, and the like have been developed for medical use. For example, intravascular devices are commonly used that are adapted to facilitate navigation through the vasculature of a patient to a treatment site. Because the vasculature of a patient may be very tortuous, it can be desirable to combine a number of performance features in such devices. For example, it can be desirable that a medical device have a relatively high level of pushability and torqueability, particularly near its proximal end. It can also be desirable that a medical device be relatively flexible, particularly near its distal end. A number of different medical device structures and assemblies are known, each having certain advantages and disadvantages. However, there is an ongoing need to provide alternative medical device structures and assemblies.

SUMMARY

The invention provides alternative designs, materials and methods of manufacturing medical device structures and assemblies. In at least some embodiments, these medical devices include an elongate shaft and an alternative design for a distal tip assembly. These and other desirable features are described in greater detail below.

BRIEF DESCRIPTION OF THE DRAWINGS

The invention may be more completely understood in consideration of the following detailed description of various embodiments of the invention in connection with the accompanying drawings, in which:

FIG. 10 is a perspective view of a distal assembly in accordance with another example embodiment.

Figure 1:
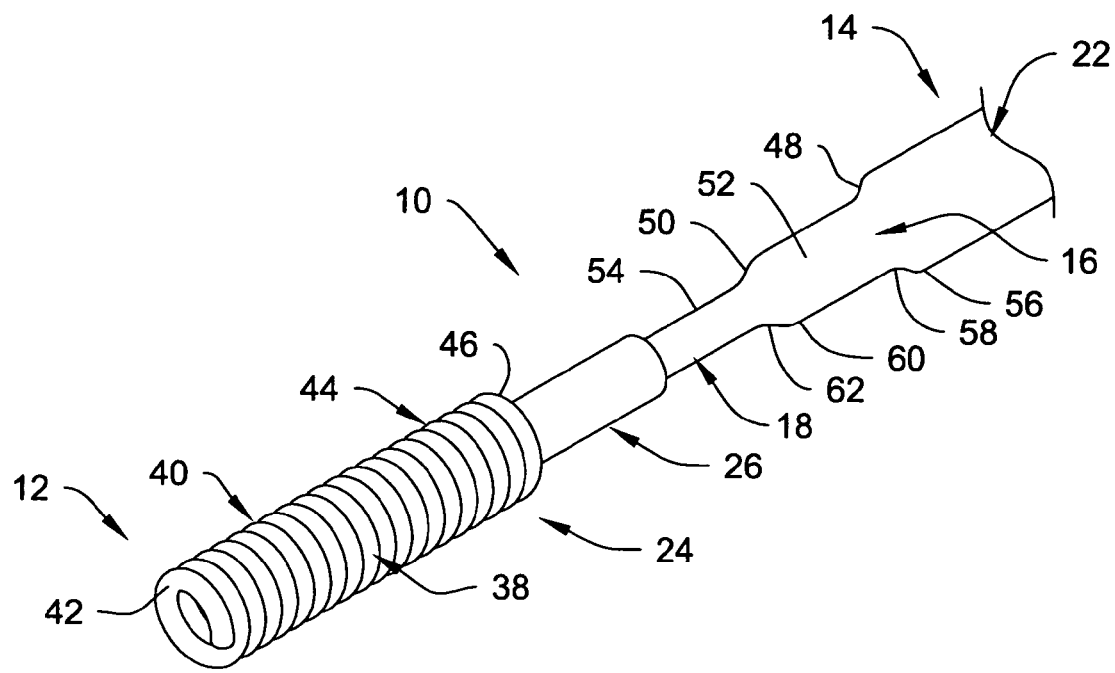
FIG. 1 is a schematic partial perspective of a portion of a core wire including a distal assembly in accordance with an example embodiment.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

Defined Terms

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Detailed Description of Some Embodiments

In at least some embodiments, the invention relates to a medical device including an alternative distal assembly adapted for use on a distal portion of an elongated shaft or core member. In some embodiments, the alternative tip assembly includes a tubular member adapted for connection to a distal end of a core member. A coil member is connected to the tubular member, and can extend distally beyond the distal end of the core member.

The following description should be read with reference to the drawings wherein like reference numerals indicate like elements throughout the several views. The detailed description and drawings illustrate examples of various embodiments of the claimed invention, and are not intended to be limiting. For example, although discussed with specific reference to guidewires in the particular embodiments discussed below, the invention may be applicable to almost any medical device having a tip designed to pass through an opening or body lumen. For example, the invention may be applicable to intravascular catheters (e.g., balloon catheters, stent delivery catheters, etc.), intravascular rotational devices (atherectomy catheters, IVUS catheters, etc.), fixed wire devices, endoscopic devices, laproscopic devices, embolic protection devices, or the like, or any other suitable device.

Figure 2:
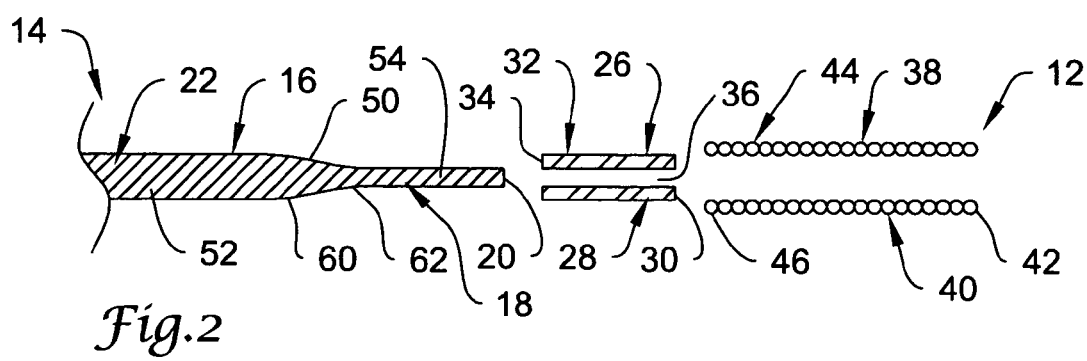
FIG. 2 is a schematic exploded side view of the core wire and distal assembly of FIG. 1.
Figure 3:
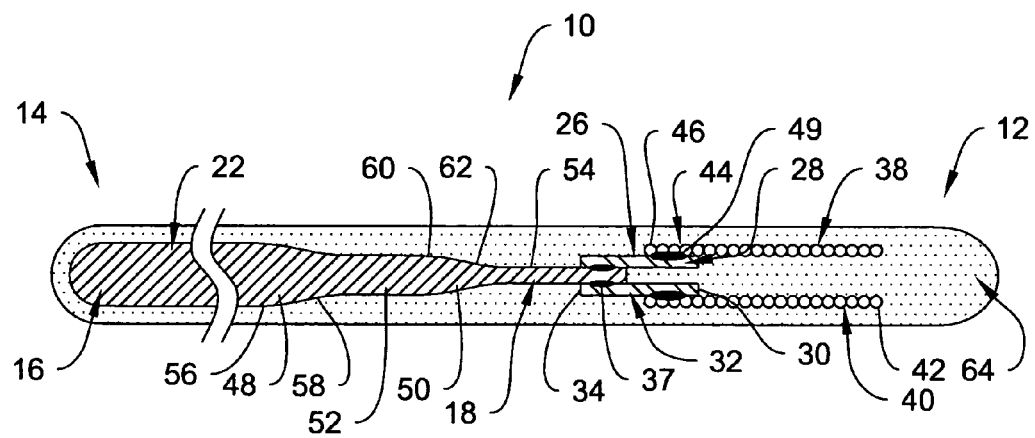
FIG. 3 is a schematic cross sectional view of a guidewire incorporating the core wire and distal assembly of FIG. 1 and further showing an outer polymer sheath.

Refer now to FIGS. 1-3, which illustrate a portion of an example embodiment of a guidewire 10 that includes a distal portion 12 and a proximal portion 14. As used herein, the distal and proximal portions 12 and 14 can generically refer to any two adjacent sections along any portion of the guidewire 10. The guidewire 10 also includes a core member 16 having a distal portion 18 defining a distal end 20 and a proximal portion 22. The guidewire 10 also includes a distal assembly 24 disposed over at least part of the distal portion 18 of the core member 16.

The distal assembly 24 includes a tubular member 26 having a distal portion 28 defining a distal end 30 and a proximal portion 32 defining a proximal end 34. The distal assembly 24 also includes a member or structure 38 that has a distal portion 40 defining a distal end 42 and a proximal portion 44 defining a proximal end 46. In other embodiments to be discussed in greater detail hereinafter, the tubular member 26 and member 38 can be integrally formed as a single element.

In the embodiment shown, the member 38 is a coiled structure, such as an inner coil, or a coiled shaping and/or safety structure. However, in other embodiments, the member 38 may include another non-coiled structure, such as a wire or ribbon, such as a shaping and/or safety wire or ribbon. In some embodiments, the proximal end 42 of the coil member 38 can be configured to fit over the distal end 30 of the tubular member 26. In particular, the proximal portion 44 of the coil member 38 can be configured to be disposed over the distal portion 28 of the tubular member 26.

In some embodiments, the distal end 30 of the tubular member 26 can extend distally beyond the distal end 20 of the core member 16. In some embodiments, the distal end 42 of the coil member 38 can extend distally beyond the distal end 30 of the tubular member 26. In particular embodiments, the proximal end 46 of the coil member 38 can be positioned proximal of, proximate to, or even distal of the distal end 20 of the core member 16.

The proximal portion 44 of the member 38 can be secured to the distal portion 28 of the tubular member 26 using any suitable attachment means. Illustrative attachment means include welding, soldering, brazing, crimping, heat bonding, adhesive bonding, mechanical bonding, the use of an expandable alloy, or the like. Some example embodiments of techniques and structures used to connect different structures in medical devices are disclosed in U.S. patent application Ser. No. 09/972,276 now U.S. Pat. No. 6,918,882, and Ser. No. 10/086,992 entitled "COMPOSITE GUIDEWIRE" filed on Feb. 28, 2002, both of which are incorporated herein by reference. Some additional examples of suitable interconnection techniques are disclosed in a U.S. patent application Ser. No. 10/375,766 entitled "COMPOSITE MEDICAL DEVICE" filed on Feb. 26, 2003, and Ser. No. 10/376,068 entitled "ELONGATED INTRACORPORAL MEDICAL DEVICE", filed on Feb. 26, 2003, both of which are also incorporated herein by reference. In some particular embodiments, laser welding can be employed to attach the coil member 38 to the tubular member 26, resulting in welds 49 (FIG. 3).

The tubular member 26 defines a lumen or opening 36 that, in the illustrated embodiment, extends through the length of the tubular member 26. In other embodiments, the lumen 36 can extend through only a portion of the length of the tubular member 26. For example, the lumen 36 can extend from the proximal end 34 of the tubular member 26 through only a portion of the length of the member 26. The lumen 36 can be adapted to receive the distal end 20 of the core member 16 for connection to the distal end 20 of the core member 16. In some embodiments, the tubular member 26 may define an inner surface that extends about the outer perimeter of the opening or lumen defined therein, for example, as shown in FIGS. 1-3. In other embodiments, the tubular member may include portions thereof wherein the inner surface extends only partially about the outer perimeter of the opening, for example, as in the embodiments discussed below with reference to FIGS. 5-9.

As illustrated, the tubular member 26 is largely cylindrical in shape, although other geometries are contemplated. For example, while the illustrated embodiment shows a circular cross section (see FIG. 1), the tubular member 26 can have a square cross section, or a polygonal cross section such as an octagonal cross section. In some embodiments, the tubular member 26 can be obtained by cutting a proper length from a tubular stock of the appropriate material. The tubular member 26 can be created and/or formed using any of a variety of techniques, for example, it may be extruded, cold-drawn, cast, molded, or the like. In some embodiments, the tubular member 26 can have an overall length that is in the range of about 0.02 inches to about 0.5 inches, an inner diameter that is in the range of about 0.005 inches to about 0.025 inches, and an outer diameter that is in the range of about 0.007 inches to about 0.038 inches.

In some embodiments, it can be useful to first attach the tubular member 26 to the core member 16, followed by subsequently attaching the coil member 38 to the tubular member 26. In other embodiments, it can be useful to first attach the coil member 38 to the tubular member 26, thereby forming the distal assembly 24. The distal assembly 24 can subsequently be attached to the core member 16. Therefore, in some embodiments, the distal assembly 24 can be a prefabricated assembly, for example, wherein the member 38 is attached to the tubular member 26. In such embodiments, the distal assembly 24 can thereafter be connected to another portion of a medical device, for example, to the distal end of the core member 26.

As illustrated for example in FIG. 1, the tubular member 26 can fit over the distal end 20 of the core member 16. The proximal end 34 of the tubular member 26 can be secured to the core member 16 using any suitable means, for example, those discussed above with regard to attachment of the coil member 38 to the tubular member 26. In some embodiments, the proximal portion 32 of the tubular member 26 can be configured to be disposed over the distal portion 18 of the core member 16.

In some embodiments, the proximal end 34 of the tubular member 26 can be secured to the core member 16 using welding techniques such as laser welding, or using soldering techniques such as laser diode soldering. In particular embodiments, the proximal end 34 of the tubular member 26 can be secured to the core member via laser welding, resulting in welds 37 (FIG. 3). In some embodiments, the distal end 30 of the tubular member 26 can extend distally of the distal end 20 of the core member 16.

It is to be appreciated that various welding processes may be utilized without deviating from the spirit and scope of the present invention. Examples of welding processes which may be suitable in some applications include LASER welding, resistance welding, TIG welding, microplasma welding, electron beam, and friction or inertia welding. LASER welding equipment which may be suitable in some applications is commercially available from Unitek Miyachi of Monrovia, Calif. and Rofin-Sinar Incorporated of Plymouth, Mich. Resistance welding equipment which may be suitable in some applications is commercially available from Palomar Products Incorporated of Carlsbad, Calif. and Polaris Electronics of Olathe, Kans. TIG welding equipment which may be suitable in some applications is commercially available from Weldlogic Incorporated of Newbury Park, Calif. Microplasma welding equipment which may be suitable in some applications is commercially available from Process Welding Systems Incorporated of Smyrna, Tenn.

The tubular member 26 can be formed of any suitable materials including metals, metal alloys, polymers, such as high performance polymers, or the like, or combinations or mixtures thereof. Some examples of suitable metals and metal alloys include stainless steel, such as 304V, 304L, and 316L stainless steel; nickel-titanium alloy, such as linear elastic or superelastic (i.e., pseudoelastic) nitinol; nickel-chromium alloy, nickel-chromium-iron alloy, cobalt alloy, tungsten, tungsten alloy, tantalum or tantalum alloys, gold or gold alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), Elgiloy, hastelloy; monel 400; inconel 625; or the like; or other suitable material, or combinations or alloys thereof. In some embodiments, the tubular member 26, or other portions and/or sections of the guidewire, may include a material that is suitable for use in certain connection techniques. For example, in some embodiments, the tubular member may include a material that can be welded to both stainless steel and nitinol.

The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL). In some embodiments, nitinol alloys can include in the range of about 50 to about 60 weight percent nickel, with the remainder being essentially titanium. It should be understood, however, that in other embodiment, the range of weight percent nickel and titanium, and/or other trace elements may vary from these ranges. Within the family of commercially available nitinol alloys, are categories designated as "superelastic" (i.e. pseudoelastic) and "linear elastic" which, although similar in chemistry, exhibit distinct and useful mechanical properties.

In some embodiments, a superelastic alloy, for example a superelastic nitinol can be used to achieve desired properties. Such alloys typically display a substantial "superelastic plateau" or "flag region" in its stress/strain curve. Such alloys can be desirable in some embodiments because a suitable superelastic alloy can provide structure that exhibits some enhanced ability, relative to some other non-superelastic materials, of substantially recovering its shape without significant plastic deformation, upon the application and release of stress, for example, during insertion or navigation of the guidewire in the body.

In some other embodiments, a linear elastic alloy, for example a linear elastic nitinol can be used to achieve desired properties. For example, in some embodiments, certain linear elastic nitinol alloys can be generated by the application of cold work, directional stress, and heat treatment, such that the material fabricated does not display a substantial "superelastic plateau" or "flag region" in its stress/strain curve. Instead, in such embodiments, as recoverable strain increases, the stress continues to increase in a somewhat linear relationship until plastic deformation begins. In some embodiments, the linear elastic nickel-titanium alloy can be an alloy that does not show any martensite/austenite phase changes that are detectable by DSC and DMTA analysis over a large temperature range. For example, in some embodiments, there may be no martensite/austenite phase changes detectable by DSC and DMTA analysis in the range of about −60° C. to about 120° C., and in other embodiments, in the range of about −100° C. to about 100° C. The mechanical bending properties of such material are therefore generally inert to the effect of temperature over a broad range of temperature. In some particular embodiments, the mechanical properties of the alloy at ambient or room temperature are substantially the same as the mechanical properties at body temperature. In some embodiments, the use of the linear elastic nickel-titanium alloy can provide for structure that exhibits superior "pushability" around tortuous anatomy. One example of a suitable nickel-titanium alloy exhibiting at least some linear elastic properties is FHP-NT alloy commercially available from Furukawa Techno Material Co. of Kanagawa, Japan. Additionally, some examples of suitable nickel-titanium alloy exhibiting at least some linear elastic properties include those disclosed in U.S. Pat. Nos. 5,238,004 and 6,508,803, which are incorporated herein by reference.

In at least some embodiments, portions or all of the tubular member 26 can be doped with, made of, or otherwise include a radiopaque material. Radiopaque materials are understood to be materials capable of producing a relatively bright image on a fluoroscopy screen or another imaging technique during a medical procedure. This relatively bright image aids the user of device in determining its location. Some examples of radiopaque materials can include, but are not limited to, gold, platinum, palladium, tantalum, tungsten alloy, polymer material loaded with a radiopaque filler, and the like.

In some embodiments, a degree of MRI compatibility can be imparted. For example, to enhance compatibility with Magnetic Resonance Imaging (MRI) machines, it may be desirable to make the tubular member 26 in a manner that would impart a degree of MRI compatibility. For example, the tubular member 26, or portions thereof, can be made of a material that does not substantially distort the image and create substantial artifacts (artifacts are gaps in the image). Certain ferromagnetic materials, for example, may not be suitable because they may create artifacts in an MRI image. The tubular member 26, or portions thereof, may also be made from a material that the MRI machine can image. Some materials that exhibit these characteristics include, for example, tungsten, Elgiloy, MP35N, nitinol, and the like, and others.

The coil member 38 can be made of a variety of materials including metals, metal alloys, polymers, and the like. Some examples of material for use in the coil include those discussed above with regard to the tubular member 26.

In some embodiments, the coil member 38 can be made of a radiopaque material and/or may be formed of materials or include structure that is MRI-compatible, as described with respect to the tubular member 26.

The coil member 38 can be formed of round or flat ribbon ranging in dimensions to achieve the desired flexibility. In some embodiments, the coil member 38 can be a round ribbon in the range of about 0.001-0.015 inches in diameter, and can have a length in the range of about 0.1 to about 4 inches.

The coil member 38 can be wrapped in a helical fashion by conventional winding techniques. The pitch of adjacent turns of the coil member 38 can be tightly wrapped so that each turn touches the succeeding turn or the pitch may be set such that the coil member 38 is wrapped in an open fashion. The pitch can be constant throughout the length of the coil member 38, or it can vary, depending upon the desired characteristics such as flexibility. In the embodiment shown, the coil member 38 is wrapped such that the coil member 38 has a closed pitch.

In some embodiments, the coil member 38 can have a pitch of up to about 0.4 inches, in some embodiments a pitch of up to about 0.08 inches, and in some embodiments, a pitch in the range of about 0.01 to about 0.08 inches. Changes in coil pitch can be achieved during the initial winding of the wire, or can be achieved by manipulating the coil after winding or after attachment to the guidewire.

In some embodiments, the diameter of the coil member 38 can be sized to fit around and mate with the distal portion 28 of the tubular member 26, and to give the desired characteristics. The diameter of the coil member 38 can be constant or tapered.

Those of skill in the art and others will recognize that the materials, structure, and dimensions of the core member 16 are dictated primary by the desired characteristics and function of the final guidewire, and that any of a broad range of materials, structures, and dimensions can be used.

The core member 16 can be made of any and all suitable materials including metals, metal alloys, polymers, or the like, or combinations or mixtures thereof. Some examples of suitable materials include those discussed above with regard to the tubular member. In some embodiments, the core member 16 or any portion thereof may include, be coated or plated with, or otherwise include a radiopaque material and/or may include material and/or structure that imparts a degree of MRI compatibility as described above.

The entire core member 16 can be made of the same material, or in some embodiments, can include portions or sections made of different materials. In some embodiments, the material used to construct core member 16 is chosen to impart varying flexibility and stiffness characteristics to different portions thereof. For example, the proximal region 20 and the distal region 18 can be formed of different materials, for example materials having different moduli of elasticity, resulting in a difference in flexibility.

In some embodiments, the material used to construct the proximal portion 22 can be relatively stiff for pushability and torqueability, and the material used to construct the distal portion 18 can be relatively flexible by comparison for better lateral trackability and steerability. For example, the proximal portion 22 can be formed of stainless steel wire or ribbon, and the distal portion 18 can be formed of a super elastic or linear elastic alloy, for example a nickel-titanium alloy wire or ribbon.

In embodiments where different portions of core member 16 are made of different material, the different portions can be connected using any suitable connecting techniques. For example, the different portions can be connected using welding, soldering, brazing, adhesive, or the like, or combinations thereof. Additionally, some embodiments can include one or more mechanical connectors or connector assemblies to connect the different portions of the core wire tat are made of different materials. The connector may include any structure generally suitable for connecting portions of a guidewire. One example of a suitable structure includes a structure such as a hypotube or a coiled wire which has an inside diameter sized appropriately to receive and connect to the ends of the proximal portion 22 and the distal portion 18. Some other examples of suitable techniques and structures that can be used to interconnect different shaft sections are disclosed in U.S. patent application Ser. No. 09/972,276 now U.S. Pat. No. 6,918,882, and Ser. No. 10/086,992 entitled "COMPOSITE GUIDEWIRE" filed on Feb. 28, 2002, both of which are incorporated herein by reference. Some additional examples of suitable interconnection techniques are disclosed in a U.S. patent application Ser. No. 10/375,766 entitled "COMPOSITE MEDICAL DEVICE" filed on Feb. 26, 2003, and Ser. No. 10/376,068 entitled "ELONGATED INTRACORPORAL MEDICAL DEVICE", filed on Feb. 26, 2003, both of which are also incorporated herein by reference.

The length of the core member 16, or the length of individual portions thereof, are typically dictated by the length and flexibility characteristics desired in the final medical device. In some example embodiments, the proximal portion 22 can have a length in the range of about 20 to about 300 centimeters and distal portion 18 can have a length in the range of about 3 to about 50 centimeters. It can be appreciated that alterations in the length of the core member 16 or portions thereof can be made without departing from the spirit of the invention. In addition, the core member 16 can have a solid cross-section as shown, but in some embodiments, can have a hollow cross-section and/or be generally tubular. In yet other embodiments, the core member 16 can include a combination of areas having solid cross-sections and hollow cross sections. Moreover, the core member 16 or portions thereof, can be made of rounded wire, flattened ribbon, or other such structures having various cross-sectional geometries. The cross sectional geometries along the length of the core member 16 can also be constant or can vary.

The core member 16 can include one or more tapered portions, for example proximate the distal portion 18. For example, in some embodiments the distal portion 18 can be tapered and have an initial outside size or diameter that can be substantially the same as the outside diameter of the proximal portion 22, which then tapers to a reduced size or diameter. The core member 16 can be linearly tapered, tapered in a curvilinear fashion, uniformly tapered, non-uniformly tapered, or tapered in a step-wise fashion. The angle of any such tapers can vary, depending upon the desired flexibility characteristics. The length of the taper may be selected to obtain a more (longer length) or less (shorter length) gradual transition in stiffness. It can be appreciated that essentially any portion of the core member 16 can be tapered and the taper can be in either the proximal or the distal direction. The number, arrangement, size, and length of the narrowing and constant diameter portions can be varied to achieve the desired characteristics, such as flexibility and torque transmission characteristics.

In some embodiments, the core member 16 can have a proximal portion 22 having a diameter that is in the range of about 0.035 inches to about 0.05 inches. The distal portion 18 of the core member 16 can include one or more tapers. In the embodiment illustrated, the distal portion 18 of the core member 16 can include a first tapered portion 48, a second tapered portion 50 and an intervening first constant diameter portion 52. A second constant diameter portion 54 can be positioned proximate to but extending distally of the second tapered portion 50.

In some embodiments, for example, the first tapered portion 48 can have a diameter that is in the range from about 0.009 inches to about 0.035 inches at a proximal end 56 to a diameter that is in the range of about 0.005 inches to about 0.025 inches at a distal end 58 and a length in the range of about 0.01 inches to about 0.5 inches. Similarly, the second tapered portion 50 can have a diameter that is in the range from about 0.005 inches to about 0.025 inches at a proximal end 60 to a diameter that is in the range of about 0.003 inches to about 0.02 inches at a distal end 62 and a length in the range of about 0.01 inches to about 0.5 inches. The constant diameter portion 52 can have a diameter in the range of about 0.005 inches to about 0.025 inches, and a length in the range of about 0.05 inches to about 0.5 inches.

The tapered regions 48 and 50 and constant diameter portion 52, or any portion thereof can be formed by any one of a number of different techniques, for example, by centerless grinding methods, stamping methods, and the like. The centerless grinding technique may utilize an indexing system employing sensors (e.g., optical/reflective, magnetic) to avoid excessive grinding of the connection. In some embodiments, the core member 16 can be centerless ground using a Royal Master HI-AC centerless grinder. Some examples of suitable grinding methods are disclosed in U.S. patent application Ser. No. 10/346,698 entitled "IMPROVED STRAIGHTENING AND CENTERLESS GRINDING OF WIRE FOR USE WITH MEDICAL DEVICES" filed Jan. 17, 2003, which is herein incorporated by reference.

In some particular embodiments, the proximal portion 22 can be formed from a stainless steel wire having a diameter in the range of 0.01 to 0.02 inches, and a length in the range of about 50 to about 110 inches, and the distal portion 16 can be formed from a linear elastic nickel-titanium alloy, for example, nitinol wire having a diameter that ranges from a diameter to match the diameter of the proximal portion 22 to as small as about 0.002 inches, and a length in the range of 3 to 15 inches. One example of a suitable nickel-titanium alloy is FHP-NT alloy commercially available from Furukawa Techno Material Co. of Kanagawa, Japan.

With reference to FIG. 3, a guidewire 10 in accordance with some embodiments of the invention can include a polymer sheath 64. In some embodiments, the polymer sheath 64 can be disposed over the tubular member 26, the coil member 38 and at least a portion of the core member 16. In the illustrated embodiment, the polymer sheath 64 is disposed over the entirety of the core member 16, however, in other embodiments, the polymer sheath 64 may be disposed over only a distal portion of the core member 16.

Suitable material for use as the polymer sheath 64 include any material that would give the desired strength, flexibility or other desired characteristics. Some suitable materials include polymers, and like material. Examples of suitable polymer material include any of a broad variety of polymers generally known for use as guidewire polymer sleeves. The use of a polymer for the polymer sheath 64 can serve several functions. The use of a polymer sleeve can improve the flexibility properties of the distal portion 12. Choice of polymers for the polymer sheath 64 will vary the flexibility. For example, polymers with a low durometer or hardness will make a very flexible or floppy tip. Conversely, polymers with a high durometer will make a tip which is stiffer. In some embodiments, the polymer sheath 64 can include different sections having different flexibility characteristics. For example, in some embodiments, the polymer sheath 64 may include a distal section made of a more flexible material, and one or more proximal sections made of a less flexible material. It should be understood that the flexibility characteristics of different sections of the polymer sheath may vary as desired. The use of polymers for the sleeve can also provide a more atraumatic tip for the guide wire. An atraumatic tip is suited for passing through fragile body passages. Finally, a polymer can act as a binder for radiopaque materials, as discussed in more detail below.

In some embodiments, the polymer material used is a thermoplastic polymer material. Some examples of some suitable materials include polyurethane, elastomeric polyamides, block polyamide/ethers (such as Pebax), silicones, and copolymers. The sleeve may be a single polymer, multiple layers, or a blend of polymers. By employing selection of materials and processing techniques, thermoplastic, solvent soluble, and thermosetting variants of these materials can be employed to achieve the desired results.

The polymer sheath 64 can be disposed around and attached to the guidewire 10 using any suitable technique for the particular material used. In some embodiments, the polymer sheath 64 is attached by heating a sleeve of polymer material to a temperature until it is reformed around the guidewire 10. In some other embodiments, the polymer sheath 64 can be attached using heat shrinking, extrusion, casting, molding, dipping, or other such techniques. The polymer sheath 64 can be finished, for example, by a centerless grinding or other method, to provide the desired diameter and to provide a smooth and/or textured outer surface as desired.

In some embodiments, the polymer sheath 64, or portions thereof, can include, or be doped with, radiopaque material to make the polymer sheath 64, or portions thereof, more visible when using certain imaging techniques, for example, fluoroscopy techniques. Any suitable radiopaque material known in the art can be used. Some examples include precious metals, tungsten, barium subcarbonate powder, or the like, or mixtures thereof. In some embodiments, the polymer sheath 64 can include different sections having different amounts of loading with radiopaque material. In some embodiments, it is also contemplated that a separate radiopaque member or a series of radiopaque members, such as radiopaque coils, bands, tubes, or other such structures could be attached to the guidewire 10, or incorporated into the core wire by plating, drawing, forging, or ion implantation techniques.

Additionally, in some embodiments, a coating, for example a lubricious (e.g., hydrophylic) or other type of coating may be applied over portions or all of the polymer sheath 64, or other portions of the guidewire 10. Hydrophobic coatings such as fluoropolymers provide a dry lubricity which improves guide wire handling and device exchanges. Lubricious coatings improve steerability and improve lesion crossing capability. Suitable lubricious polymers are well known in the art and may include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference. In some embodiments, the more distal portion of the guidewire is coated with a hydrophilic polymer as discussed above, and the more proximal portions is coated with a fluoropolymer, such as polytetrafluroethylene (PTFE).

Figure 4:
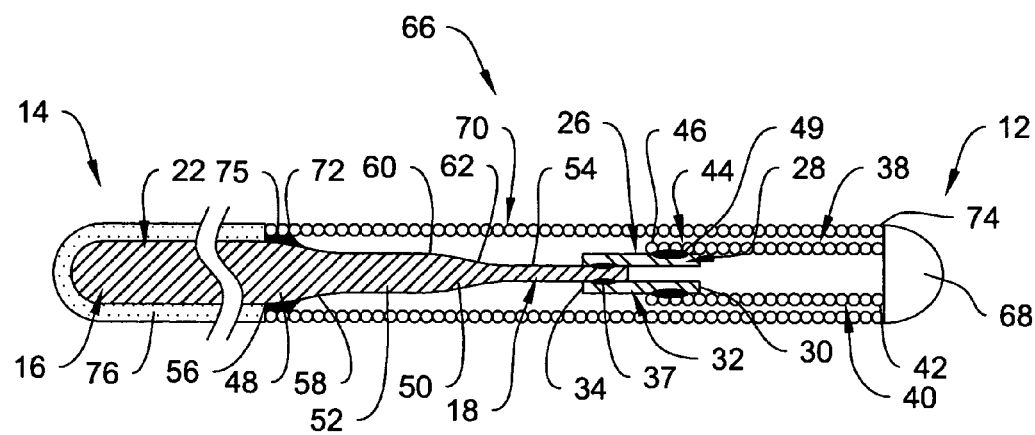
FIG. 4 is a schematic cross sectional view of a portion of another guidewire including a core wire and distal assembly as in FIG. 1, and further including an outer coil in accordance with another example embodiment.

Turning now to FIG. 4, another example embodiment is illustrated. FIG. 4 shows a guidewire 66 that includes a core member 16 as described above with respect to FIGS. 1-3. The guidewire 66 also includes a tubular member 26 and a coil member 38, also as described above with respect to FIGS. 1-3. This particular embodiment adds several features, however. An atraumatic tip 68 is positioned proximate the distal end 42 of the coil member 38.

The atraumatic tip 68 can be formed of any suitable metallic or non-metallic material. In some embodiments, the atraumatic tip 68 can be formed of materials that are MRI compatible, as discussed with respect to the tubular member 26. In particular embodiments, the atraumatic tip 68 can be formed from a material that is amenable to soldering or welding. For example, in some embodiments, the tip 68 is a solder tip.

A coil 70, having a proximal end 72 and a distal end 74, can be disposed over the core member 16 and the coil member 38. In some embodiments, the distal end 74 of the coil 70 can be secured to the atraumatic tip 68 using any suitable attachment means such as welding, soldering, brazing, adhesive bonding, mechanical bonding, or the like. In some embodiments, the proximal end 72 of the coil 70 can be secured to the core member 16. For example, in the embodiment shown, the coil 70 is secured to the core 16 proximate the proximal end 56 of the first taper portion 48. Connection can be made using any suitable attachment means such as those discussed above. In some embodiments, the proximal end 72 of the coil 70 can be laser welded to the core member 16, resulting in welds 75. It should be understood, however, that these attachment points are given by way of example only, and that the coil 70 can be attached at different locations and by using more or fewer attachment points, as desired, without parting from the spirit and scope of the invention. For example, in some other embodiments, the distal end 74 may be attached to other structure, for example, a spacer member or attachment or centering ring, or may be free of attachment. Additionally, the coil 70 can be attached at one or more intermediate points, for example, to the centering or attachment ring. For example, a centering ring could be used that functions to attach the coil 70 to the core member 16, and can also function to somewhat maintain the axial and lateral position of the coil 70 relative to the core member 16. Additionally, in other embodiments, the coil 70 can be disposed at other locations along the length of the guidewire 66, or could extend the entire length of the guidewire 66.

As illustrated in FIG. 4, a polymer sheath or coating 76 can be disposed over the proximal portion 22 of the core member 16. The polymer sheath or coating 76 can be formed of any suitable polymeric or coating material and can be attached as described above with respect to the polymer sheath 64 and/or coatings discussed above. While not specifically illustrated, the polymer sheath 76 can extend to cover part or all of the core member 16 and/or may extend over all or a portion of coil 70.

Figure 5:
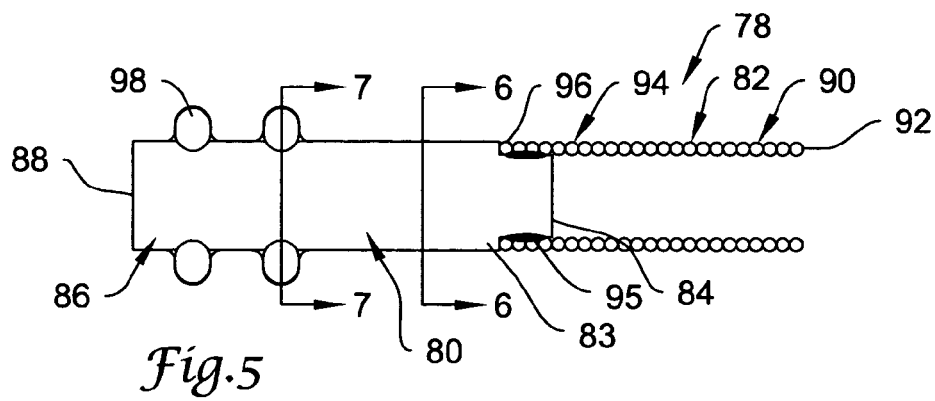
FIG. 5 is a schematic cross sectional view of a portion of a distal assembly in accordance with another example embodiment.
Figure 6:
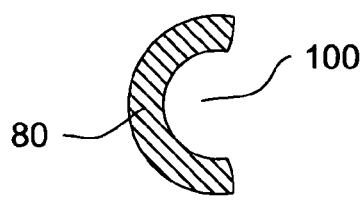
FIG. 6 is a schematic cross sectional view taken along line 6-6 of FIG. 5.

Turning now to FIGS. 5-9, another example embodiment is illustrated. FIG. 5 shows a distal assembly 78. The distal assembly 78 can include a tubular member 80 and a coil member 82. The tubular member 80 has a distal portion 83 defining a distal end 84 and a proximal portion 86 defining a proximal end 88. The tubular member 80 includes a lumen 100 that can be configured to accept a core member. In this embodiment, the tubular member 80 defines an inner surface that extends about only a portion of the opening or lumen 100, and defines a half-moon or half-pipe type shape. In other embodiments, the tubular member 80 may extend around more or less of the opening or lumen 100 than shown. The coil member 82 has a distal portion 90 defining a distal end 92 and a proximal portion 94 defining a proximal end 96.

The tubular member 80 can form part or all of a cylindrical shape. As illustrated for example in FIG. 6, the tubular member 80 can have a hemispherical cross section. In some embodiments, a hemispherical cross section has manufacturing advantages as the partial tubular member 80 can be moved radially onto a core member, as opposed to being slid axially over a core member.

Figure 7:
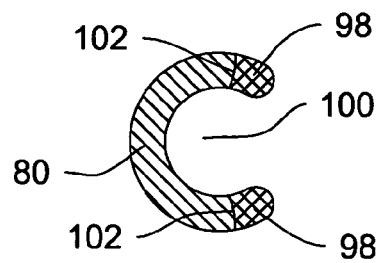
FIG. 7 is a schematic cross sectional view taken along line 7-7 of FIG. 5.

The member 80 can include one or more securement tabs 98. As seen in FIG. 7, the securement tabs 98 can be configured such that they extend from a tubular member edge 102. In some embodiments, the securement tabs 98 can be adapted and/or configured to be bent around a core member once the tubular member 80 has been axially aligned with the core member.

The tubular member 80 can be formed from any suitable materials including metals, metal alloys, polymers, or the like, or combinations or mixtures thereof, for example, those discussed above with regard to tubular member 26. As discussed with respect to the tubular member 26, the tubular member 80 can be formed from or include radiopaque materials and may include structure or material for MRI compatibility.

The coil member 82 can be made of a variety of materials including metals, metal alloys, polymers, and the like, for example, the materials discussed with regard to coil member 38 and tubular member 26. Additionally, coil member 82 can be made or formed, and include structure similar to that discussed above with regard to the coil member 38. As discussed with respect to the coil member 38, the coil member 82 can be formed from or include radiopaque materials and may include material or structure for MRI compatibility. Additionally, while the embodiment shown includes a coiled member 38, other non-coiled structure may be used in place of a coil. For example, a shaping and/or safety ribbon or wire may be attached to the tubular member 80 in place of and/or in addition to the coil member 82.

In some embodiments, the proximal portion 94 of the coil member 82 can be configured to fit over the distal end 84 of the tubular member 80. The proximal portion 94 of the coil member 80 can be secured to the distal portion 82 of the tubular member 80 using any suitable attachment means. Illustrative attachment means can include welding, soldering, brazing, adhesive bonding, mechanical bonding, and the like. In particular embodiments, laser welding can be employed, resulting in welds 95.

In some embodiments, it can be useful to first attach the tubular member 80 to the core member 16 (see FIG. 8), followed by subsequently attaching the coil member 82 to the tubular member 80. In other embodiments, it can be useful to first attach the coil member 82 to the tubular member 80, thereby forming the distal assembly 78. The distal assembly 78 can subsequently be attached to the core member 16 (see FIG. 8). Therefore, in some embodiments, the distal assembly 78 can be a prefabricated assembly which can be thereafter connected to another portion of a medical device, such as the core member 16.

Figure 8:
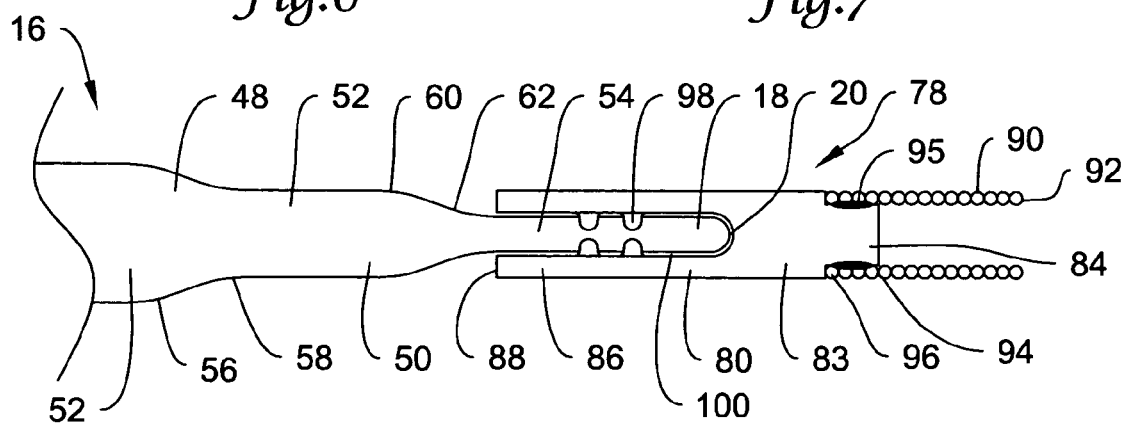
FIG. 8 is a schematic cross sectional view of a guidewire including the distal assembly of FIG. 5.
Figure 9:
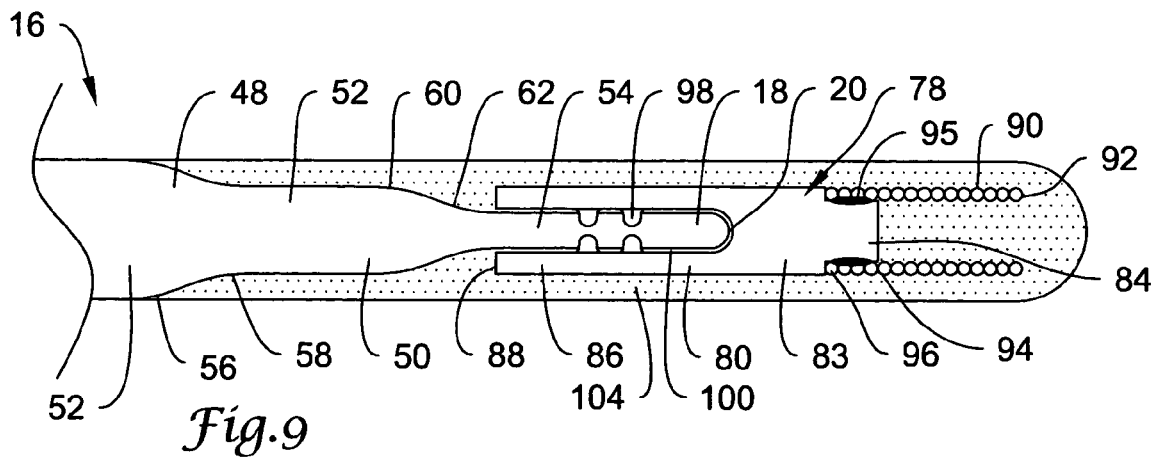
FIG. 9 is a schematic cross sectional view of the guidewire of FIG. 8, further including a polymer sleeve.

FIGS. 8 and 9 illustrate uses of the distal assembly 78. In FIG. 8, the distal assembly 78 has been fitted over the core member 16. The core member 16 is as previously described with respect to FIGS. 1-3. In particular, the core member 16 includes a distal constant diameter portion 54 that includes the distal end 20 thereof. The distal assembly 78 can be disposed over the distal constant diameter portion 54 such that the distal constant diameter portion 54 fits within the lumen 100. Once the core member 16 and the distal assembly 78 have been aligned, the securement tabs 98 can be bent over the core member 16 to help secure the distal assembly 78 to the core member 16. In some embodiments, additional attachment techniques such as welding, soldering, brazing, adhesive bonding, mechanical bonding, the use of an expandible alloy, such as a bismuth alloy, or the like, can be used to further secure the distal assembly 78, in addition to the mechanical means provided by the securement tabs 98.

FIG. 9 is similar to FIG. 8, but illustrates the addition of a polymer sheath 104. The polymer sheath can be formed from any suitable polymeric material, such as discussed with respect to the polymer sheath 64.

It should be understood that distal tip assemblies in accordance with the invention can be used and/or incorporated into a broad variety of medical device constructions, and that the above embodiments are provided by way of example only. Some examples of additional medical device constructions are shown and described in U.S. patent application Ser. No. Ser. No. 09/972,276 now U.S. Pat. No. 6,918,882, 10/086,992 entitled "COMPOSITE GUIDEWIRE" filed on Feb. 28, 2002; Ser. No. 10/375,766 entitled "COMPOSITE MEDICAL DEVICE" filed on Feb. 26, 2003; and Ser. No. 10/376, 068 entitled "ELONGATED INTRACORPORAL MEDICAL DEVICE", filed on Feb. 26, 2003, all of which are incorporated herein by reference.

In the preceding discussion, the distal assembly 24 has been formed by connecting or otherwise joining the tubular member 26 and the member 38 (see FIGS. 1-4). The distal assembly 78 has been formed by connecting or otherwise joining the tubular member 80 and the coil member 82 (see FIGS. 5-9). However, in some embodiments it is possible to provide both the tubular member 26 or 80 and the member 38 (or coil member 82) integrally formed as a single element. FIG. 10 is a perspective view of a distal assembly 106.

In particular, the distal assembly 106 has a proximal portion 108 including a proximal end 110, and a distal portion 112 including a distal end 114. The distal assembly 106 includes a tubular section 114 positioned proximate the proximal portion 108 and a flexible section 116 that extends from the tubular section 114 to at least the distal portion 112. In some embodiments, the flexible section 116 extends distally to the distal end 114. As illustrated, the tubular section 114 defines a closed lumen 118 much like the lumen 36 (FIG. 2) that extends at least partially through the tubular member 26. In other embodiments, however, the tubular section 114 can have a cross-section profile that does not define a closed lumen, much like the cross-section of the tubular member 80 (FIG. 5) as illustrated for example in FIG. 6.

In some embodiments, the distal assembly 106 can be formed from tubular stock, much as discussed previously with respect to the tubular member 26. The distal assembly 106 can be formed from any suitable materials including metals, metal alloys, polymers, or the like, or combinations or mixtures thereof, for example, those discussed above with regard to the tubular member 26. As discussed with respect to the tubular member 26, the distal assembly 106 can be formed from or include radiopaque materials and may include structure or material for MRI compatibility.

The flexible portion 116 can be formed by removing appropriate portions of the tubular stock. In some embodiments, the flexible portion 116 can be formed by laser cutting the tubular stock to form a void 118 between adjacent turns 120. In some embodiments, as illustrated, the voids 118 can be sized and dimensioned to provide an open pitch to the flexible portion 116. In other embodiments, the voids 118 can simply be slits that provide the flexible portion 116 with a closed pitch.

Once the distal assembly 106 has been formed, it can be attached to a core member 16 as described with respect to distal assembly 24 and distal assembly 78. In particular, the tubular section 114 can be secured to the distal end 20 of the core member 16 using welding techniques such as laser welding, or using soldering techniques such as laser diode soldering. In some embodiments, the distal assembly 116 can be mechanically secured to the distal end 20 of the core member 16.

It should be understood that this disclosure is, in many respects, only illustrative. Changes may be made in details, particularly in matters of shape, size, and arrangement of steps without exceeding the scope of the invention. For example, alternative structure can be used in connecting the proximal and distal sections of guidewires. Additionally, alternative tip constructions including a flexible coil tip, a polymer jacket tip, a tip including a coiled safety/shaping wire, or combination thereof, and other such structure may be placed on the guidewire. The invention's scope is, of course, defined in the language in which the appended claims are expressed.

We claim:

1. A guidewire, comprising:
   a metallic core member having a proximal end and a distal end, wherein the core member is generally solid in cross-section;
   a metallic tubular member having a proximal end and a distal end disposed around and attached to the distal end of the core member; and
   a metallic coil member disposed about and attached to the distal end of the tubular member and
   an outer member connected to the core member proximal of the proximal end of the tubular member and disposed around the core member, tubular member and metallic coil member,
   wherein the tubular member has a uniform inner diameter and a uniform outer diameter and wherein the distal end of the core member where the tubular member is attached has an outer diameter that is substantially the same as the inner diameter of the tubular member and wherein the coil member has an inner diameter that is greater than the outer diameter of the tubular member, and
   wherein the tubular member extends distally beyond the distal end of the core member and the coil member extends distally beyond the distal end of the tubular member.

2. The guidewire of claim 1, wherein a proximal end of the coil member is positioned proximate to or distal of the distal end of the core member.

3. The guidewire of claim 1, wherein the proximal end of the tubular member fits over the distal end of the core member.

4. The guidewire of claim 1, wherein the outer member is a polymer sheath disposed over all of the core member.

5. The guidewire of claim 1, wherein the tubular member is connected to the core member through laser welding or laser diode soldering.

6. The guidewire of claim 1, wherein the tubular member is connected to the core member through mechanical fastening means.

7. The guidewire of claim 1, wherein the tubular member is connected to the core member through crimping.

8. The guidewire of claim 7, wherein the coil member is connected to the tubular member through laser welding.

9. The guidewire of claim 1, wherein the tubular member has a hemispherical cross section.

10. The guidewire of claim 1, wherein the tubular member has a circular cross section.

11. The guidewire of claim 1, wherein the outer member is a polymer sheath disposed about the coil member, the tubular member, and at least a portion of the core member.

12. The guidewire of claim 1, wherein the tubular member has a C-shaped cross section.

13. The guidewire of claim 1, wherein a proximal end of the coil is distal the distal end of the core member.

14. The guidewire of claim 1, wherein a proximal end of the coil is distal the proximal end of the tubular member.

* * * * *